(12) United States Patent
Gardner

(10) Patent No.: US 11,129,822 B2
(45) Date of Patent: Sep. 28, 2021

(54) TREATING OF SIDE-EFFECTS RESULTING FROM CHEMODENERVATION

(71) Applicant: DELNOVA, INC., Highland Park, IL (US)

(72) Inventor: Mary Gardner, Highland Park, IL (US)

(*) Notice: Subject to any disclaimer, the term of this patent is extended or adjusted under 35 U.S.C. 154(b) by 0 days.

(21) Appl. No.: 16/099,581

(22) PCT Filed: May 15, 2017

(86) PCT No.: PCT/US2017/032636
§ 371 (c)(1),
(2) Date: Nov. 7, 2018

(87) PCT Pub. No.: WO2017/197382
PCT Pub. Date: Nov. 16, 2017

(65) Prior Publication Data
US 2019/0183875 A1 Jun. 20, 2019

Related U.S. Application Data

(60) Provisional application No. 62/336,344, filed on May 13, 2016.

(51) Int. Cl.

| | |
|---|---|
| *A61K 31/455* | (2006.01) |
| *A61K 31/27* | (2006.01) |
| *A61K 31/4425* | (2006.01) |
| *A61K 31/55* | (2006.01) |
| *A61K 31/407* | (2006.01) |
| *A61P 21/02* | (2006.01) |
| *A61K 9/00* | (2006.01) |
| *A61K 9/06* | (2006.01) |
| *A61K 9/70* | (2006.01) |
| *A61K 47/24* | (2006.01) |
| *A61K 31/445* | (2006.01) |

(52) U.S. Cl.
CPC .......... *A61K 31/455* (2013.01); *A61K 9/0019* (2013.01); *A61K 9/0053* (2013.01); *A61K 9/06* (2013.01); *A61K 9/7023* (2013.01); *A61K 31/27* (2013.01); *A61K 31/407* (2013.01); *A61K 31/445* (2013.01); *A61K 31/4425* (2013.01); *A61K 31/55* (2013.01); *A61K 47/24* (2013.01); *A61P 21/02* (2018.01)

(58) Field of Classification Search
CPC .. A61K 31/27; A61K 31/407; A61K 31/4425; A61K 31/445; A61K 31/455; A61K 31/55; A61K 9/0019; A61K 9/0053; A61K 9/06; A61K 9/7023; A61K 47/24; A61P 21/02
See application file for complete search history.

(56) References Cited

U.S. PATENT DOCUMENTS

| | | | | |
|---|---|---|---|---|
| 4,925,856 A | * | 5/1990 | Harris, III ............ | C07D 233/64 514/161 |
| 5,622,976 A | * | 4/1997 | Takasugi .............. | C07D 271/06 514/305 |
| 6,165,500 A | * | 12/2000 | Cevc ...................... | A61K 9/127 424/450 |
| 6,759,552 B2 | * | 7/2004 | Shivanandappa ....... | C07C 65/40 562/474 |
| 2002/0068699 A1 | * | 6/2002 | Donovan ................. | C07K 7/22 514/18.3 |
| 2008/0090808 A1 | * | 4/2008 | Volvovitz ........... | A61K 31/4709 514/214.03 |
| 2009/0068242 A1 | * | 3/2009 | Carlier ................... | A01N 47/22 424/409 |
| 2015/0191480 A1 | * | 7/2015 | Bai ..................... | C07D 491/056 514/252.03 |

FOREIGN PATENT DOCUMENTS

| | | | | |
|---|---|---|---|---|
| CN | 1542125 A | * | 11/2004 | |
| CN | 101386818 A | * | 3/2009 | |
| WO | WO-2011046411 A3 | * | 9/2011 | .......... A61K 31/192 |
| WO | WO-2014039920 A1 | * | 3/2014 | |
| WO | WO-2015195928 A1 | * | 12/2015 | .......... A61K 31/683 |

OTHER PUBLICATIONS

Thwaites, Medicine, 2014, Elsevier, vol. 42:1, pp. 11-13 (Year: 2014).*
Watters et. al., Current Treatment Options in Neurology, 2004, Current Science, vol. 6, pp. 115-123 (Year: 2004).*
Adler et. al., Toxicon, 1996, Pergamon, vol. 34(2), pp. 237-249 (Year: 1996).*
O'Connor, et al., "Pharmcology of Neuromascular Blocking Drugs and Aticholnesterases", World Anaesthesia Tutorial of the Week; Anaesthesia UK, First available online: May 6, 2006 (currently available at https://www.frca.co.uk/article.aspx?articleid=100642).
"Highlights of Prescribing Information", a.k.a., package insert, for Botox. Allergan, Inc. Version released Jan. 2006.
"Cholinestersase Inhibitors & Other Pharmacologic Antagonists to Neuromascular Blocking Agents", Morgan & Mikhail's Clinical Anesthesiology, Chapter 12 (summary), 5th edition, (currently available at https://accessmedicine.mhmedical.com/content.aspx?bookid=564&sectionid=42800543).
"Mechanism of Action" Allergan, Inc. Botox Prescribing Information, Mar. 2010.

(Continued)

*Primary Examiner* — Sarah Pihonak
(74) *Attorney, Agent, or Firm* — McDonnell Boehnen Hulbert & Berghoff LLP

(57) ABSTRACT

The present disclosure relates generally to methods of restoring neuromuscular transmission by locally administering an effective dose of a composition comprising an anticholinesterase to a non-responsive muscle. The disclosure also relates to methods of reversing a neurotoxin-induced muscle paralysis or muscle weakness, the method comprising locally administering a composition comprising an anticholinesterase to the patient.

26 Claims, 3 Drawing Sheets

(56) References Cited

OTHER PUBLICATIONS

Marchini, et al., "Intranasal neostigmine therapy of botulinum toxin (BTX) treatment dysphagia", Clinical Neurapharmacology, 20:279-282 (1997).
Young, et al., "Pyridostigmine for Reversal of Severe Sequelae From Botulinum Toxin Injection", Journal of Boise, 28:830-834 (2014).
Colovic, et al., "Acetylcholinesterase inhibitors: pharmacology and toxicology", Current Neuropharmacology, 11:315-335 (2013).
De Paiva, et al., "Functional repair of motor endplates after botulinum neurotoxin type A poisoning: biphasic switch of synaptic activity between nerve sprouts and their parent terminals", Proc. Natl. Acad. Sci., 96:3200-3205 (1999).
Gage, "Preclinical Toxicology of New Drugs", Battelle Report, 8740-86-2, (1986).
Moon, et al., "Early effect of Botox-A injection into the masseter muscle of rats: functional and histological evaluation", Maxillofacial Plastic and Reconstructive Surgery, 37:46 (2015).
Rhee, et al., "Sustained-Release Injectable Drug Delivery", Pharmaceutical Technology, 2010:1-7 (2010).
Srivastava, et al, "Reversal of Neuromascular Block", British Journal of Anasthesia, 103:115-29 (2009).
Nair, "Anticholinesterases and anticholinergic drugs", Continuing Education in Anaesthesia, Critical Care & Pain, 4:164-168 (2004).
McEvoy GK, ed., "Pyridostigmine bromide", AFS Drug Information, 1249-1252 (2007).
Alnasser, et al., "A Review on Nasal Drug Delivery System and Its Contribution in Therapeutic Management", Asian Journal of Pharmaceutical and Clinical Research, 12:40-45 (2019).
Ushkaryov, et al., "α-Latrotoxin and Its Receptors", Handb Exp. Pharmacol., 184:171-206 (2008).
Ural, et al., "The comparison of analgesic effects of various administration methods of diclofenac sodium, transdermal, oral and intramuscular, in early postoperative period in laparoscopic cholecystectomy operations", Pak J Med Sci., 30:96-100 (2014).
Burden, et al., "Acetylcholine receptors at neuromuscular synapses: Phylogenetic differences detected by snake α-neurotoxins", Proc. Nat. Acad. Sci., 72:3245-3249 (1975).
Duregotti, et al., "Snake and Spider Toxins Induce a Rapid Recovery of Function of Botulinum Neurotoxin Paralysed Neuromuscular Junction", Toxins, 7:5322-5336 (2015).
Aracava, et al., "Effectiveness of Donepezil, Rivastigmine and (+) Huperzine A in Counteracting the Acute Toxicity of Organophosphorus Nerve Agents: Comparison with Galantamine", Journal of Pharmacology and Experimental Therapeutics, 331:1014-1024 (2009).
Greenberg et al., "The Use of Neuromolecular Blocking Agents in the ICU: Where Are We Now"? Crit. Care Med, 41(5)1332-1344 (2013).
Fiekers, "Concentration-dependent effects of neostigmine on the endplate acetylcholine receptor channel complex", The Journal of Neuroscience, 5:502-14 (1985).
Elmaki, et al., "Potential Molecular Docking of Four Acetylcholinesterase Inhibitors". Drug Designing & Intellectual Properties International Journal, 191-194 (2018).
Yu, et al., "Long-acting anticholnesterases for myasthenia gravis: synthesis and activities of quaternary phenylcarbamates of neostigmine, pyridostigmine and physostigmine", Bioorg Med Chem., 18:4687-4693 (2010).
Poulain, et al., "Cellular and Molecular Mode of Action of Botulinum and Tetanus Neurotoxins", Advances in Organ Biology, 2:285-313 (1997).

\* cited by examiner

Figure 1

TREATING OF SIDE-EFFECTS RESULTING FROM CHEMODENERVATION

CROSS-REFERENCE TO RELATED APPLICATIONS

This application claims the benefit of U.S. Provisional Patent Application No. 62/336,344, filed May 13, 2016, which is incorporated herein by reference in their entireties.

BACKGROUND OF THE DISCLOSURE

1. Field of the Disclosure

The present disclosure relates generally to methods of restoring neuromuscular transmission by locally administering an effective dose of a composition comprising an anticholinesterase to a non-responsive muscle. The disclosure also relates to methods of treating a neurotoxin-induced muscle paralysis or muscle weakness, the method comprising locally administering a composition comprising an anticholinesterase to the patient.

2. Technical Background

Botulinum toxin has been used for treatment of over 20 medical and cosmetic indications. Botulinum toxin is a nerve impulse "blocker." It attaches to nerve endings and prevents the release of chemical transmitters, which activate muscles. These chemicals carry the "message" from the brain that tells a muscle to contract. If the message is blocked, the muscle does not contract.

Local administration of botulinum toxin is targeted to achieve muscle relaxation and not muscle immobility or complete block. But the effects of botulinum toxin may, in some cases, be observed beyond the site of local injection and is referred to as spread of toxin effect. Side effects of botulinum toxin can be potentially life threatening and some cases temporarily disfiguring. Temporary but disfiguring side effects include "droopy eyelids" (eyelid ptosis), which results from the neurotoxin infiltrating into the muscle that raises the eyelid or other unintended fascial muscle side effects known as, "frozen face," "arched or droopy brow," puffiness or swelling of lips, and in some cases pain or muscle weakness, as related to medical procedures. There is currently no approved product available for the treatment (e.g., rescue) of the effects of botulinum toxin.

SUMMARY OF THE DISCLOSURE

The present inventor has found that peripherally (i.e., locally) acting anticholinesterase can be used as a neurotoxin rescue agent.

Botulinum toxins act presynaptically to block the release or exocytosis of acetylcholine (ACh) from the synapse (FIG. 1). Once botulinum toxin is injected into the muscle, the neurotoxin is taken up into the nerve terminal. It prevents binding of the synaptic vesicle containing the acetylcholine by cleaving SNAP-25, a protein that is crucial for docking of the vesicle to the nerve ending. Thus, neurotransmitter release into the synaptic cleft is inhibited and muscle contraction cannot occur.

Studies have shown the ability of nerve endings at the neuromuscular junction to sprout following blockade of neurotransmission by botulinum neurotoxin. The sprouting which occurs following intoxication of the motor nerve terminals by botulinum toxin has the ability to form functional synapses as they present with key proteins that are necessary for exocytosis. The sprouts are formed to release ACh and induce electrical activity (de Paiva et al. (1999) *Proc. Natl. Acad. Sci.* 96(6): 3200-3205). Although the factors involved in triggering this outgrowth are not completely understood, there is evidence to show that the sprouts eventually decay once the original nerve activity is restored. The synaptic ACh concentrations may be increased by inhibiting degradation that would normally take place, via the acetylcholinesterase (AChE). AChE is a potent enzyme which triggers rapid degradation of ACh. The acetylated enzyme is hydrolyzed rapidly while free enzyme and acetic acid are formed. Approximately 10 000 molecules of acetylcholine are hydrolyzed per second in each active site (Ĉolović et al. (2013) *Current Neuropharmacology* 11(3): 315-335).

Non-depolarizing neuromuscular blocking drugs (NMBDs) bind to the receptor as a competitive antagonist thus blocking the binding of ACh and preventing its ability to depolarize the receptor. The non-depolarizing NMBDs do not effect a conformational change in the receptor. Botulinum toxins are considered to be non-depolarizing, however, as compared to NMBDs, they have a different mechanism of action. There is no competitive blocking at the AChE receptor sites. Nevertheless, without the binding of ACh, the ACh receptors are trapped in a desensitized state.

ACh diffuses across membrane, binds to receptor at motor endplate and triggers muscle action potential. AChE in synaptic cleft destroys ACh and breaks into acetate and choline. Choline is then reabsorbed to synthesize new ACh. Cholinesterase inhibitor (also known as anticholinesterase) acts indirectly by inactivating AChE. Specifically, the cholinesterase inhibitor breaks down AChE in synaptic cleft so it cannot attack existing molecules of ACh. Delivering an anticholinesterase/cholinesterase inhibitor into the synaptic cleft will extend the life of the ACh thereby increasing its concentration, and making it available to bind at the ACh receptor. Timing for the administration is important as in its use in anesthesia, "antagonism of neuromuscular block with an anticholinesterase should not be attempted until two twitches of the train-of-four twitch response are detectable, otherwise it will be ineffective" (Srivastava and Hunter (2009) *British Journal of Anesthesia*, 103(1):1115-29). This guidance suggests the need to wait for evidence of recovery from induced neuromuscular block. In order for the recovery to occur, ACh needs to be present. In the case of botulinum toxin poisoned terminals this points to a pre-condition of partial block or the spontaneous recovery of neuromuscular function following the action of a neuromuscular blocker requires an increase in the concentration of acetylcholine.

The inventor has found that targeted, localized parenteral administration of an anticholinesterase to the affected patient reverses/alleviates/treats muscle chemical denervation, such as that caused by botulinum toxin administration. The targeted administration of the anticholinesterase (for example, by using a low dose) to the afflicted tissue/muscle reverses the unintended effects. The methods outlined herein minimize potential for systemic side effects, such as those resulting from first pass metabolism in oral dosage forms or side effects from higher intravenous dosages. Furthermore, the use of targeted drug delivery allows for reversal of the impaired areas, without impacting the principle areas that were originally targeted for therapy.

Thus, in one aspect, the present disclosure provides methods of restoring neuromuscular transmission by locally administering an effective dose of a composition comprising an anticholinesterase to a non-responsive muscle.

In another aspect, the present disclosure provides methods of treating a neurotoxin-induced (e.g., a botulinum toxin induced) muscle paralysis or muscle weakness, the method comprising locally administering a composition comprising an anticholinesterase to the patient.

BRIEF DESCRIPTION OF THE DRAWINGS

The accompanying drawings are included to provide a further understanding of the methods and devices of the disclosure, and are incorporated in and constitute a part of this specification. The drawings illustrate one or more embodiment(s) of the disclosure, and together with the description serve to explain the principles and operation of the disclosure.

Figure 1:
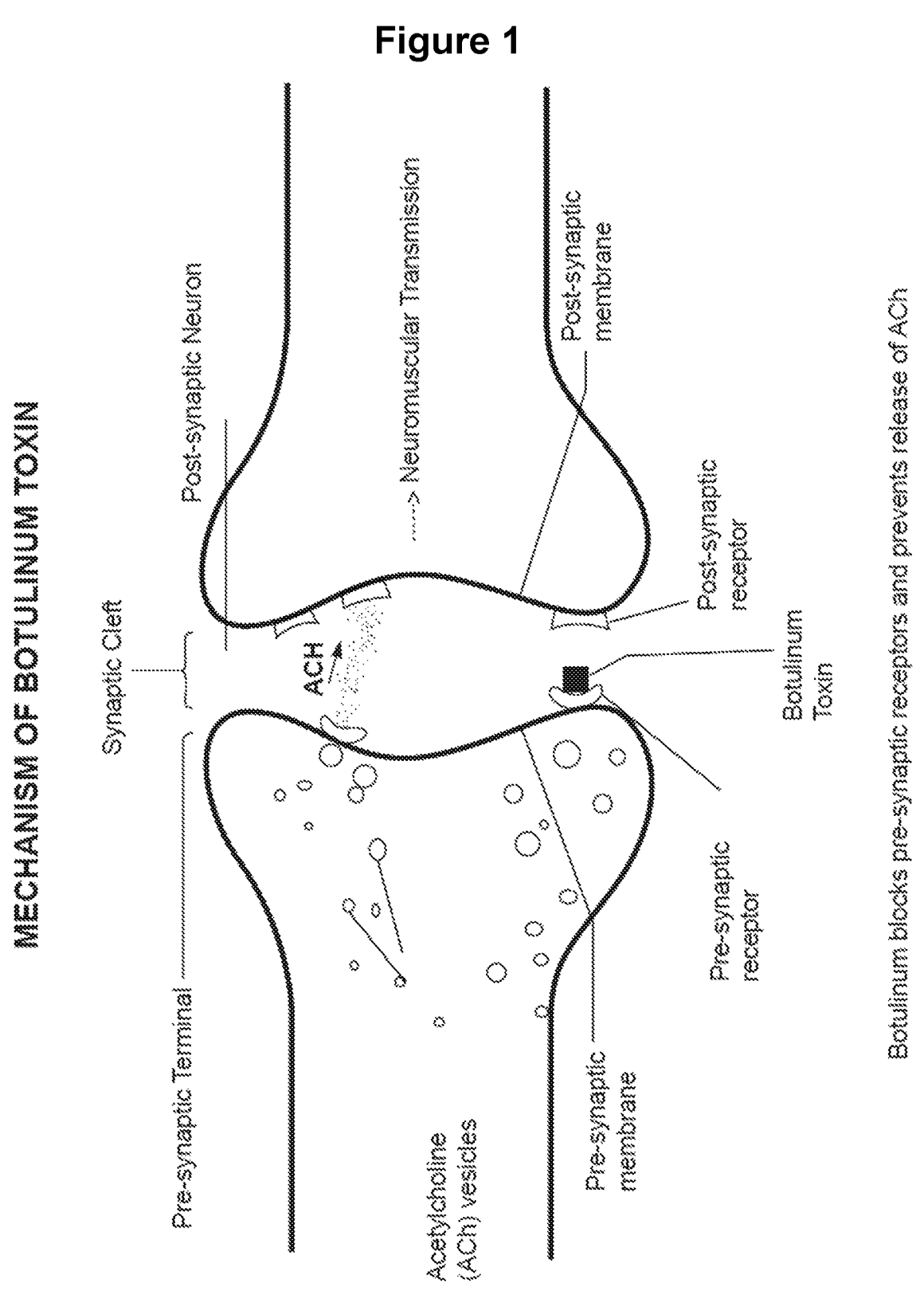

FIG. 1 illustrates botulinum toxin mechanism of action.

DETAILED DESCRIPTION

Figure 2:
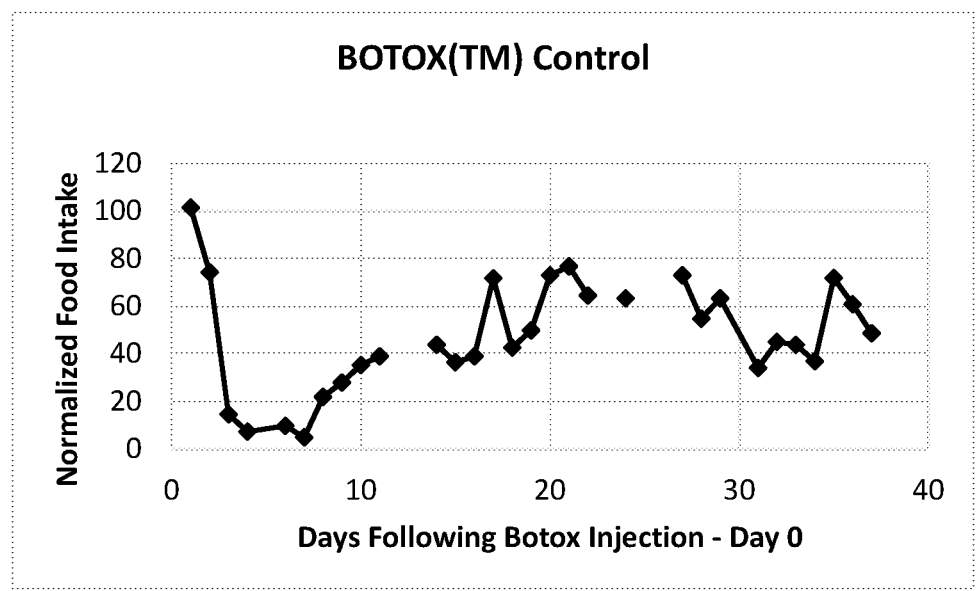
FIG. 2 shows the food intake of rats treated with BOTOX only (i.e., no treatment with an anticholinesterase).

Before the disclosed methods and materials are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

An "effective amount" refers to that amount of a compound which, when administered to a subject, is sufficient to effect treatment for condition described herein. The amount of a compound which constitutes an "effective amount" will vary depending on the compound, the disorder and its severity, and the age of the subject to be treated, but can be determined routinely by one of ordinary skill in the art.

The term "muscle paralysis" as used herein means a complete loss of muscle function. Muscle paralysis may be accompanied by a loss of feeling (sensory loss) in the affected area.

The term "muscle weakness" as used herein means a partial loss of muscle function and/or loss of muscle strength.

The term "chemical denervation" or "chemodenervation" as used herein means loss of nerve supply (i.e., block of neural transmission) caused by an agent (e.g., chemical compound).

In view of the present disclosure, the methods and active materials described herein can be configured by the person of ordinary skill in the art to meet the desired need. In general, the disclosed materials, methods, and apparati provide targeted, localized parenteral administration of an anticholinesterase to the affected patient to restore neuromuscular transmission in a drug-induced non-responsive muscle.

The neurotoxin botulinum is used in a broad range of cosmetic and medical procedures. Temporary, but undesirable side effects result from the inadvertent spread of toxin into adjacent muscle structures, causing paralysis or weakness in unintended areas. The neurotoxin acts to block the release of ACh, at the neuromuscular junction. The anticholinesterase acts to indirectly increase ACh by degrading the endogenous AChE. The binding of ACh to its receptor sites is necessary to maintain muscle transmission. The depth of block is a critical factor which dictates the efficacy of the anticholinesterase in accelerating spontaneous recovery. In order for recovery or muscle reactivation to occur, ACh needs to be present. As used herein, the term "depth of the block" refers to the level of occupancy of postsynaptic receptors.

Due to the nature of paralysis and spread induced by botulinum toxin in commercial use, partial chemical denervation and/or natural recovery will occur. Therefore, the condition or depth of block will determine the speed of recovery. The present inventor has found that peripherally acting anticholinesterase can be used as a neurotoxin rescue agent accelerating the time to recovery. The inventor has found that the timing of dosing of anticholinesterase, the concentration of anticholinesterase, and period of dosing are important elements in the efficacy of the rescue treatment.

Thus, in one aspect, the present disclosure provides methods of restoring neuromuscular transmission by locally administering an effective dose of a composition comprising an anticholinesterase to a non-responsive muscle. In certain embodiments, the non-responsive muscle has been previously exposed to a neurotoxin. In certain embodiments, the non-responsive muscle has been previously exposed to a botulinum toxin.

In another aspect, the present disclosure provides methods of treating a neurotoxin-induced muscle paralysis or muscle weakness, the method comprising locally administering a composition comprising an anticholinesterase to the patient. In certain embodiments, the neurotoxin in a botulinum toxin.

The botulinum toxin is a neurotoxic protein produced by *Clostridium botulinum* and related species. Strains of *Clostridium botulinum* produce seven distinct neurotoxins designated as types A-G. All seven types have a similar structure and molecular weight, consisting of a heavy (H) chain and a light (L) chain joined by a disulphide bond and they all interfere with neural transmission by blocking the release of acetylcholine. Therefore, in one embodiment, botulinum toxin of the disclosure includes one or more of Type A, Type B, Type C, Type D, Type E, Type F, and Type G. In one embodiment, the botulinum toxin of the disclosure includes one or more of Type A, Type B, Type E, and Type F. In one embodiment, the botulinum toxin of the disclosure includes one or more of Type A and Type B. In one embodiment, the botulinum toxin of the disclosure is botulinum toxin Type A.

Botulinum toxin Type A is approved for use by the FDA for use in cosmetic procedures, and is available under various brand names, one of which is BOTOX® (Allergan, Irvine, Calif., USA; herein "BOTOX"). Similarly, botulinum toxin is also used to treat over 20 medical conditions. The most common medical conditions include migraines, excessive sweating, muscle spasms, urinary incontinence, etc. The spread of toxin away from the injection site or overuse of the toxin can cause unwanted side effects in such procedures. For example, in the treatment of migraines, neck pain is the most common side effect, experienced by approximately 9% of people in the botulinum toxin group vs 3% in placebo group.

The methods of the disclosure require a composition comprising an anticholinesterase. Anticholinesterases (i.e., cholinesterase inhibitors) fall into two classes, organophosphorus compounds, which are non-reversible, and carbamates, which are reversible. The former generally have higher toxicity, longer duration of action, and are often associated with central nervous system (CNS) toxicity. Reversible anticholinesterases have found applications in medicine for a broad range of indications. For example, some reversible anticholinesterases are used in treatment of Alzheimer's disease as these can cross the blood brain barrier to reach the CNS.

In some embodiments, the anticholinesterase of the disclosure is a reversible anticholinesterase. In some embodiments, the anticholinesterase of the disclosure is a reversible anticholinesterase having one or more of groups selected from carbamate, tertiary ammonium, and quaternary ammonium.

In some embodiments, the anticholinesterase is selected from one or more of: physostigmine, neostigmine, ambenonium, pyridostigmine, ambenonium, demecarium, rivastigmine, galantamine, donepezil, tacrine, 7-methoxytacrine, edrophonium, huperzine A, ladostigil, and any derivative and combinations thereof.

In some embodiments, the anticholinesterase of the disclosure is selected from one or more of:

neostigmine edrophonium pyridostigmine physostigmine rivastigmine donepezil galantamine and a combination thereof.

In some embodiments of the disclosure, the anticholinesterase is pyridostigmine, neostigmine, edrophonium, or a combination thereof.

In some embodiments of the disclosure, the anticholinesterase is pyridostigmine. Pyridostigmine is not lipid soluble and as such is peripherally acting. This property makes it desirable for use in muscle related conditions. Pyridostigmine is also safer as compared to neostigmine due to fewer incidences of bradycardia and arrhythmias.

In some embodiments of the disclosure, the anticholinesterase is a compound of formula (I):

(I)

or a pharmaceutically acceptable salt thereof, wherein
Y is $CR^3$ or $N^+X^-R^4$, wherein X is a halogen;
$R_1$ is selected from hydrogen, $C_1$-$C_6$ alkyl, —CO(OH), —CO($C_1$-$C_6$ alkoxy), —CO($NH_2$), —CONH($C_1$-$C_6$ alkyl), and —CON($C_1$-$C_6$ alkyl)$_2$;
$R_2$ is hydrogen, or $R_2$ and $R_3$ together with the atoms to which they are attached form an optionally substituted heterocycle;

$R_3$ is selected from $C_1$-$C_6$ alkyl, $C_1$-$C_6$ alkoxy, hydroxy $C_1$-$C_6$ alkyl, amino $C_1$-$C_6$ alkyl, ($C_1$-$C_6$ alkylamino) $C_1$-$C_6$ alkyl, (di $C_1$-$C_6$ alkylamino) $C_1$-$C_6$ alkyl, $C_1$-$C_6$ alkoxy $C_1$-$C_6$ alkyl —OH, —$NH_2$, —NH($C_1$-$C_6$ alkyl), —N($C_1$-$C_6$ alkyl)$_2$, and —$N^+$($C_1$-$C_6$ alkyl)$_3$$X^-$; and $R_4$ is selected from $C_1$-$C_6$ alkyl, hydroxy $C_1$-$C_6$ alkyl, or $C_1$-$C_6$ alkoxy $C_1$-$C_6$ alkyl.

In some embodiments, the compound of formula (I) is wherein Y is C. In some embodiments, the compound of formula (I) is wherein Y is or $N^+X^-$, or Y is $N^+Br^-$ or $N^+Cl^-$, or Y is $N^+Br^-$.

In some embodiments, the compound of formula (I) according to any one of preceding embodiments is wherein $R_1$ is selected from hydrogen, $C_1$-$C_6$ alkyl, —CO($NH_2$), —CONH($C_1$-$C_6$ alkyl), and —CON($C_1$-$C_6$ alkyl)$_2$. In some embodiments, the compound of formula (I) is wherein $R_1$ is selected from hydrogen, —CO($NH_2$), —CONH($C_1$-$C_6$ alkyl), and —CON($C_1$-$C_6$ alkyl)$_2$. In some embodiments, the compound of formula (I) is wherein $R_1$ is hydrogen. In some embodiments, the compound of formula (I) is wherein $R_1$ is —CO($NH_2$), —CONH($C_1$-$C_6$ alkyl), or —CON($C_1$-$C_6$ alkyl)$_2$. In some embodiments, the compound of formula (I) is wherein $R_1$ is —CON($C_1$-$C_6$ alkyl)$_2$.

In some embodiments, the compound of formula (I) according to any one of preceding embodiments is wherein $R_2$ is hydrogen. In some embodiments, the compound of formula (I) according to any one of preceding embodiments is wherein $R_2$ together with $R_3$ and the atoms to which they are attached form an optionally substituted heterocycle. In some embodiments, the heterocycle is optionally substituted with one or more of halogen, $C_1$-$C_6$ alkyl, $C_1$-$C_6$ haloalkyl, $C_1$-$C_6$ alkoxy, —OH, —$NH_2$, —NH($C_1$-$C_6$ alkyl), or —($C_1$-$C_6$ alkyl)$_2$. In some embodiments, the heterocycle is octahydropyrrolo[2,3-b]pyrrole or pyrrolidine, each optionally substituted with one or more of halogen, $C_1$-$C_6$ alkyl, $C_1$-$C_6$ haloalkyl, $C_1$-$C_6$ alkoxy, —OH, —$NH_2$, —NH($C_1$-$C_6$ alkyl), or —N($C_1$-$C_6$ alkyl)$_2$. In some embodiments, the heterocycle is octahydropyrrolo[2,3-b]pyrrole optionally substituted with one or more of halogen, $C_1$-$C_6$ alkyl, $C_1$-$C_6$ haloalkyl, $C_1$-$C_6$ alkoxy, —OH, —$NH_2$, —NH($C_1$-$C_6$ alkyl), or —N($C_1$-$C_6$ alkyl)$_2$.

In some embodiments, the compound of formula (I) according to any one of preceding embodiments is wherein $R_3$ is selected from $C_1$-$C_6$ alkoxy, —OH, —$NH_2$, —NH($C_1$-$C_6$ alkyl), —N($C_1$-$C_6$ alkyl)$_2$, and —$N^+$($C_1$-$C_6$ alkyl)$_3$$X^-$. In some embodiments, $R_3$ is selected from $C_1$-$C_6$ alkoxy and —OH. In some embodiments, $R_3$ is selected from —$NH_2$, —NH($C_1$-$C_6$ alkyl), —N($C_1$-$C_6$ alkyl)$_2$, and —$N^+$($C_1$-$C_6$ alkyl)$_3$$X^-$. In some embodiments, $R_3$ is —$N^+$($C_1$-$C_6$ alkyl)$_3$$X^-$. In some embodiments, $R_3$ is —$N^+$($C_1$-$C_6$ alkyl)$_3$$Br^-$ or –$N^+$($C_1$-$C_6$ alkyl)$_3$$Cl^-$.

In one embodiment, the methods of the disclosure require targeted delivery of the composition. Targeted drug delivery to the site of action can enhance drug efficacy. By increasing local active drug concentration to the afflicted tissue, while minimizing exposure to other areas of the body, drug toxicity can be reduced. Localized delivery avoids hepatic first-pass metabolism and gastrointestinal tract side effects. Furthermore, the total drug dose can be significantly lower, thereby reducing patient exposure from off-target systemic side effects. This can enable more widespread use of the anticholinesterase class of drugs and its use in a cosmetic related field as well as in other non-life threatening conditions. In one embodiment of the disclosure, the composition is administered directly to the muscle affected.

Targeted drug delivery may be achieved by means of parenteral injection using conventional techniques similar to those used in the administration of botulinum toxin, or by means of transdermal delivery, either passive or active. Passive transdermal delivery refers to topical or other conventional skin patches or gels that are used to deliver active drug through the skin barrier without a driving force or perforation. In one embodiment of the disclosure, the composition is administered parenterally (e.g., by intra-muscular injection). The parenteral delivery (e.g., the intra-muscular injection) may be to the non-responsive muscle area (i.e., where the side effects such as muscle paralysis or muscle weakness are noted) or in the muscle structures as recommended by a medical professional with in-depth knowledge of muscle features.

In one embodiment of the disclosure, the composition is administered transdermally. In one embodiment, the composition is administered in transdermal patch or transdermal gel. Transdermal drug delivery allows for drug to inter the underlying tissue via the skin surface area. Given that the highest incidence of procedures will relate to the facial area, any patch or topical formulation should remain in place for a limited amount of time to allow the patient to resume normal daily activity. Once the drug has entered into the subcutaneous space and targeted tissue or muscle, it is desirable to remove the patch and remove any obstruction. The conventional patch technology is non-invasive and usually does not require administration by a medical professional as is required with injections. One of skill in the art will recognize that the performance (drug uptake/transfer through the skin) depends primarily on drug characteristics such as molecule size, lipophilicity, drug polarity, and solubility. One of skill in the art would be able to select the appropriate surfactants and/or penetration enhancers if required for improving drug transfer. If faster onset of action is required, an active transdermal technology may be adopted (e.g. microneedles or other means of skin perforation in order to enhance the rate of delivery). Active methods include for example, iontophoresis, electroporation, mechanical perturbation, and other energy-related techniques such as ultrasound and needleless injection.

Additional methods of targeted delivery can include, but not limited to, intramuscular, intradermal, subcutaneous, or topical delivery.

Given the localized nature of targeted delivery, the effective dose of the anticholinesterase is administered in a low dose, i.e., lower than the clinical dose of the anticholinesterase when dosed for said anticholinesterase's oral or intravenous use (usually dosed for other therapeutic indication). General guidance for conversion of the oral to intravenous dose is to give patients $\frac{1}{30}$ of the oral dose. Since the targeted administration, is directly injected into the tissue, as compared to an intravenous administration, the dosing could be a low as 0.1 mg or alternatively up to $\frac{1}{10}$ of the dose necessary for reversal of muscle relaxants. The effective dose may be readily understood using a known physiological technique routinely used to assess muscle or nerve impairment. An electromyogram (EMG) measures the electrical potential generated by muscle cells when the cells are electrically activated. A needle electrode discharges quick electrical pulses to the nerve and measures the time taken for the muscle or nerve to contract. The speed of contraction is reported as the conduction velocity. The conduction velocity can be measure prior and post-injection of the reversal agent. An expected increase in the conduction velocity would be a measure of the effectiveness of the dose-response.

In certain embodiments, the low dose is about $\frac{4}{5}$ to about $\frac{1}{50}$ of the clinical dose of the anticholinesterase when dosed for said anticholinesterase's oral or intravenous use (usually dosed for other therapeutic indication). In some embodiments, the low dose is about 1/5 to about 1/50 of the oral or intravenous clinical dosing, or about 1/5 to about 1/20, or about 1/5 to about 1/10, or about 1/10 to about 1/50, or about 1/10 to about 1/50, or about 1/10 of the oral or intravenous clinical dosing.

In some embodiments of the disclosure, the anticholinesterase is administered in a dose of about 0.05-0.5 mg/kg, or in a dose of about 0.15-0.25 mg/kg, or in a dose of about 0.2 mg/kg. As known in the art regarding dosing guidance provided for botulinum toxin injections, the specific dose of an anticholinesterase may be tailored to the individual based on the size, number, and location of muscles involved, with methods such as needle electromyographic guidance or nerve stimulation as an indicator of response. For example, in the treatment of hyperhidrosis in palms, doses are tailored according to the size of the palm (e.g., $cm^2$). One of skill in the art will recognize that the dosages may be higher or lower, depending upon, among other factors, the activity of the anticholinesterase, the bioavailability of the anticholinesterase, its metabolism kinetics and other pharmacokinetic properties, the mode of administration and various other factors. One of skill in the art would also recognize that the anticholinesterase should be dosed in such manner not infiltrate or spread into systemic circulation such that it would cause unwanted side effects.

In some embodiments of the disclosure, the anticholinesterase may be administered immediately after the neurotoxin (e.g., botulinum toxin). For example, the anticholinesterase may be administered at least 1 minute, or at least 2 minutes, or at least 5 minutes, or at least 10 minutes, or at least 30 minutes after the neurotoxin. In some embodiments of the disclosure, the anticholinesterase may be administered sometime after the neurotoxin (e.g., botulinum toxin). For example, the anticholinesterase may be administered at least 1 hour, or at least 6 hours, or at least 24 hours, or at least 2 days, or at least 3 days, or at least 4 days, or at least 5 days, or at least 6 days, or at least 7 days after the neurotoxin.

For the application of anticholinesterase used to address the unwanted side effects resulting from botulinum toxin and in the absence of specific monitoring, it will be important that the drug be available during the appropriate window. In one embodiment, drug may be available when ACh is present. Therefore, presence of full block will delay the response. To determine when Ach is present, the patient may be monitored by, for example, electromyography (EMG) or other test. The appropriate treatment window may be accessed by use of a sustained-release composition. The appropriate treatment window may be accessed by use of several administrations of the composition of the disclosure. In one embodiment, the composition of the disclosure may be administered one time (i.e., in a single dose). In one embodiment, the composition of the disclosure may be administered two times, or three times, or four times, or more.

The anticholinesterase would be administered after the effects of the neurotoxin become evident to the medical practitioner or patient. In some case, it may take up to 7 days to achieve the full effect of the neurotoxin. The anticholinesterase may be used at any time following the evidence of unwanted side-effects.

In one embodiment of the disclosure, the composition is a sustained-release composition. The sustained release formulation would ensure the drug is available to act as acetylcholine becomes available. The sustained release composition should circumvent the need for multiple injections of the composition of the disclosure. It will also reduce the cost of care while providing maximum efficacy with limited patient exposure and less unwanted side effects. In certain embodiments, the sustained release formulation releases the anticholinesterase over a period of days (e.g., over a period of 1-day, or 2-day, or 3-day, or 4-day, or 5-day, or 6-day, or 7-day, or 10-day, or 14-day, or 21-day, or 30-day, or between 1-day and 14-day period, or between 1-day and 7-day period, or between 3-day and 7-day period, or between 1-day and 5-day period, or between 5-day and 7-day period) or over a period of hours (e.g., up to about 3 hours, or up to about 6 hours, or up to about 12 hours, or up to about 24 hours, or between about 3 hours and about 24 hours, or between about 3 hours and about 18 hours, or between about 3 hours and about 12 hours, or between about 3 hours and about 6 hours, or between about 6 hours and about 24 hours, or between about 6 hours and about 18 hours, or between about 6 hours and about 12 hours, or between about 12 hours and about 24 hours, or between about 18 hours and about 24 hours).

Suitable sustained-release formulations are known to one of skill in the art, and the compositions of the disclosure may be formulated in variety of ways depending on the desired drug loading, the desired drug delivery profile, and/or desired rate of release/pharmacokinetics.

The sustained-release composition of the disclosure may be any one of formulations disclosed in Rhee et al. ("Sustained-Release Injectable Drug Delivery," (2010) *Pharmaceutical Technology*, Vol. 2010 Supplement, Issue 6, pp. 1-7 source URL: http://www.pharmtech.com/sustained-release-injectable-drug-delivery), herein incorporated by reference in its entirety.

The sustained-release composition of the disclosure may be prepared by methods disclosed in the U.S. Patent Publication No. 2012/0316108, herein incorporated by reference in its entirety. These formulations are one-phase gel formulations requiring the use of phospholipids (20%-80%), preferably on the low range of phospholipid use to allow for use of syringe with a finer needle. The formulation may include pharmaceutical grade lecithins from egg or soybean as practiced for parenteral products or oils which are established for use in injectable pharmaceutical preparations. The primary dispersion may include an emulsion or suspension in the first step of formulating the phospholipid gel or may be referred to as an emulsion if oil is used. Thus, in one embodiment, the composition of the disclosure is one-phase gel composition further comprising 20 to 80% by weight of phospholipids and 0.1% to 65% by weight of water. In one embodiment, the composition of the disclosure (e.g., the one-phase gel composition) is extrudable through a needle having about 30 gauge to about 33 gauge. The sustained-release one-phase gel formulations may be prepared by method comprising: (a) mixing the components to form a primary dispersion comprising one or more phospholipid(s) and excessive water; (b) homogenizing the primary dispersion to form a nanodispersion with an average particle size of less than about 200 nm in diameter; (c) passing the nanodispersion through a 0.2 m or 0.45 micron filter; and (d) removing the excessive water to obtain the gel. In some embodiments, step c may be eliminated if the formulation is heat sterilized according to standard practice for an injectable drug.

The compositions comprising anticholinesterase may further include an appropriate carrier, excipient or diluent. The exact nature of the carrier, excipient or diluent will depend upon the desired performance for the composition, and may range from being suitable or acceptable for veterinary uses to being suitable or acceptable for human use.

The compositions comprising the anticholinesterase (s) may be manufactured by means of conventional mixing, dissolving, granulating, dragee-making, levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

The anticholinesterases may be formulated in the pharmaceutical composition per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

The compositions of the disclosure may, if desired, be presented in a ready-to-use, single-use delivery formulation (including those designed for administration by injection). This will avoid issues of cross contamination and waste. Depending on the activity of the treatment center, frequency of use of a rescue product would likely not warrant a multiple-use sterile container system such as a vial. Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer, dextrose solution, etc., before use. To this end, the anticholinesterase may be dried by any art-known technique, such as lyophilization, and reconstituted prior to use.

The injectable formulations may be deployed using a range of methodologies (either in commercial use or under development). These may include but are not limited to oil-based injections, injectable drug suspensions, injectable microspheres, or in-situ systems, excipients and polymers for drug depots which dissolve over-time. Technology selection will depend on the following major factors; drug loading within the matrix, the desired drug delivery profile, rate of release/pharmacokinetics (therapeutic window). Oil-based injectable solutions and injectable drug suspensions control the release for days to weeks while polymer-based microspheres and in-situ gels or drug depots reportedly last for months. The desired final formulation will be limiting of the bulk volume that would need to be injected or otherwise administered to a patient.

The compositions of the disclosure may, if desired, be presented in a kit. The kit may be accompanied by instructions for administration.

The compositions of the disclosure may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

EXAMPLES

Animal Model and Methods

To demonstrate the efficacy of an anticholinesterase in accelerating the spontaneous recovery following botulinum toxin injections, the rat model outlined Moon et al. (*Maxillofacial Plastic and Reconstructive Surgery* (2015) 37:46) was adopted. In this case, botulinum toxin was injected into the masseter muscle of the rat and impending changes in food intake was monitored. The goal of the experiment was to cause paralysis in the jaw muscle of the rat using the botulinum neurotoxin. This was expected to negatively impact food intake and subsequently test the ability of comparable injections of anticholinesterase to accelerate the recovery process.

The test materials were products approved for injection. The botulinum toxin, BOTOX® (Allergan, Irvine, Calif., USA;), was reconstituted to the desired dose using saline for injection. The dose of BOTOX used in the experiments was 5 Units in 100 µl. For pryridostigimine, Regonol® (Sandoz Inc., Princeton, N.J., USA) was used in a ready for injection solution (5 mg/ml).

Sprague Dawley rats of typical weight between 375-400 g were subjected to either a BOTOX control or a treatment with the anticholinesterase, pyridostigimine. Each group of rats (typically 3-5) have weight and food intake monitored for a period of approximately 1 week as a baseline measurement. Then, each receives injections of BOTOX into the masseter muscles. The rat weight and food intake are tracked over 2-4 weeks in total.

It is expected that inducing paralysis of the jaw muscles will lead to a reduction in food intake and potentially weight loss, followed by recovery as the effects of the BOTOX diminish over time. Following BOTOX administration, some groups of rats receive injections of reversal agents into the masseter muscles. Treatment groups vary in dose, dose regimen, and frequency of reversal agent administration. Each animal is briefly anesthetized using isoflurane prior to injections and daily weighing. The rats were fed with pelletized rodent diet. This differs from the Moon experiment in that pulverized feed was employed. It was considered that pelletized feed would be a more representative measure of muscle atrophy and chewing capability.

BOTOX (5 Units in 100 µl) was injected into the masseter muscle of the rats. A comparable volume of saline was injected at the start of the experiments in order to standardize injection procedures and dose delivery. Although doses lower than 5 Units per side of BOTOX were tested (0.1-2.5 Units). These lower doses did not impact food intake as compared to baseline, thus suggesting the experimental model does not exhibit a dose-response. Limitation in the animal model is suspected to contribute to a dampening effect on recovery results.

To limit the possibility of dehydration in the animals during the period of muscle paralysis and severely impacted food intake, the rats were injected into the tail vein with sterile lactated ringers' solution.

Botulinum Toxin Control

As shown in FIG. 2, the BOTOX only (i.e., no treatment with an anticholinesterase), rats do not reach 100% recovery even after a 37 day period. This is consistent with the duration of action reported by the manufacturer in the product label in that the action of the neurotoxin can last in a patient for 90+ days. However, this is inconsistent with the results shown by Moon et al. where nearly full recovery occurs spontaneously after only 10 days. Reasoning for the variation in results is likely due to a different biological potency of the neurotoxin used. BOTOX is not specifically called out in the materials and methods. The potency between different botulinum toxin Type A manufacturers is not comparable and this is clearly identified in the literature and under different manufacturer product labels.

Results: Timing of Administration

As previously explained, acceleration of spontaneous recovery/reversal is dependent upon the presence of acetylcholine at the neuromuscular junction. Anticholinesterases act to inhibit the action of the enzyme cholinesterase, in breaking down acetylcholine into its base units, choline and acetic acid. Acetylcholine is normally taken up into the synapse and regenerated through choline reprocessing.

The performed experiment demonstrated that early administration of the anticholinesterase is ineffective. The appropriate timing, i.e. timing which causes an enhanced recovery response as compared to the BOTOX control, takes place after about day 6 in our animal model (i.e., 6 days after injection of the botulinum toxin). Due to the lack of response by the AChE, and without being bound to any theory, It is possible that acetylcholine is not available until this point. It is anticipated that a more immediate response would be witnessed if the dosage of neurotoxin was low enough to sustain muscle relaxation and not total immobility. For example, a sooner time to response would be expected in the case of botulinum toxin side effects. The side effects are typically the result of spread of toxin effect or poor injection technique into the target area. It is reported that side effects may take weeks to months to resolve in human use. Also, the Product Insert for BOTOX Cosmetic states that the dosage is designed to achieve partial chemical denervation. In the cases of side effects resulting from treatments of botulinum toxin in humans, the time to response may be immediate.

Results: Potentiation of Spontaneous Recovery

Figure 3:
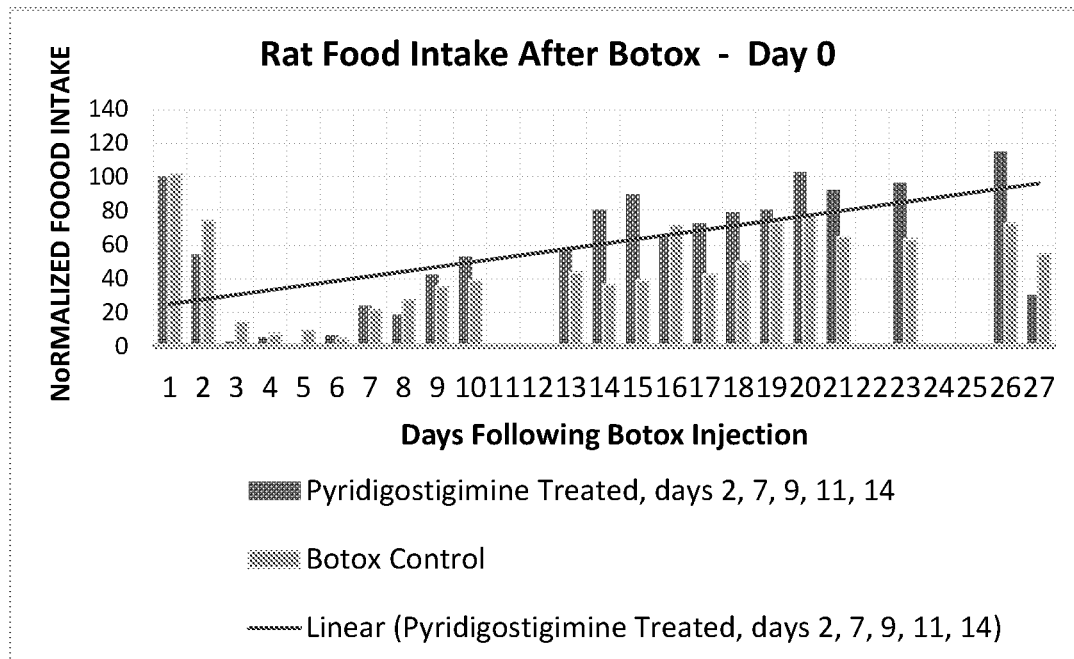
FIG. 3 shows the food intake after BOTOX injection of rats treated with an anticholinesterase on Days 2, 7, 9, 11 and 14, and rats treated with no anticholinesterase.

As shown in FIG. 3, rats were dosed with injections of Regonol® (pyridostigimine bromide) on days 2, 7, 9, 11 and 14. Dosage of Regonol® was 0.5 mg per side, 100 µl injected into the masseter muscle of the rats on the days specified. The average relative boost in food uptake was 26.3% based on data collected post-injection once the 6-day period expired.

Figure 4:
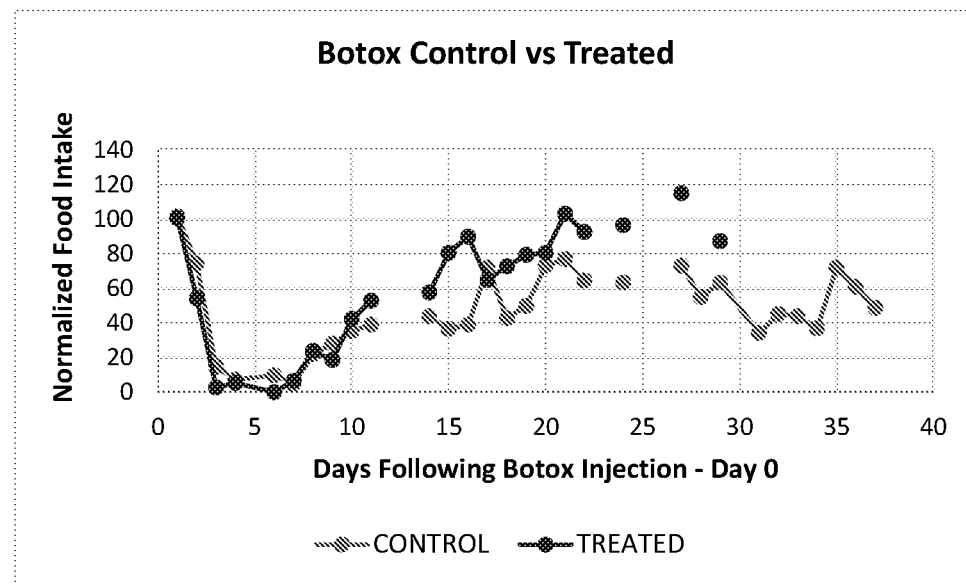
FIG. 4 is a line chart of the food intake after BOTOX injection of rats treated with an anticholinesterase on Days 2, 7, 9, 11, 14, and rats treated with no anticholinesterase.

As shown in FIG. 4, the Regonol® treated animals exhibited full recovery of food intake by approximately day 26, whereas the control animals had not yet recovered as of day 37. Also notable is that recovery continued beyond the date of the last treatment at 14 days.

Results: Poisoning of Endplates

Among the muscarinic side effects that may be observed from the dosing of an anticholinesterase are nausea, vomiting, and diarrhea. In a toxicity study for pyridostigimine in Sprague Dawley Rats, pyridostigmine-induced signs of toxicity included ocular discharge, nasal discharge, hypoactivity, prostration, ataxia, diarrhea, hunched posture, thin appearance and death (Battelle, Preclinical Toxicology of New Drugs, Report 8740-86-2, Apr. 4, 1986, J. G Gage Principle Investigator). As a result, the rats in the present example were monitored for signs of ill-effects. The rats treated by the methods of the disclosure showed no side effects.

It is important to reach an effective dosage of the anticholinesterase without effecting a poisoning of the end-plate terminals. There is no reported dosage for intramuscular injection into muscle tissue. As previously discussed, the depth of block at the time of administration will impact the effectiveness of recovery. As a parallel to the intravenous use of cholinesterase inhibition to reverse neuromuscular block at the end of anesthesia, there is no advantage to administration before the onset of spontaneous recovery. Furthermore, the cholinesterase inhibitors reach an upper limitation at higher doses. In the present animal model, it was demonstrated that giving more anticholinesterase does not induce an improved response. Without being bound to a particular theory, it could be postulated that elevated dosing could result in higher concentrations of acetylcholine at the endplate as the endogenous enzyme is not available to take away excess acetylcholine. The buildup may result in poisoning of the endplates, resulting in a constant state of depolarization. This serves as its own form of depolarization block.

As the preferred anticholinesterase has a limited duration of action, recovery will occur over time as the endogenous cholinesterase enzyme level is re-established.

Figure 5:
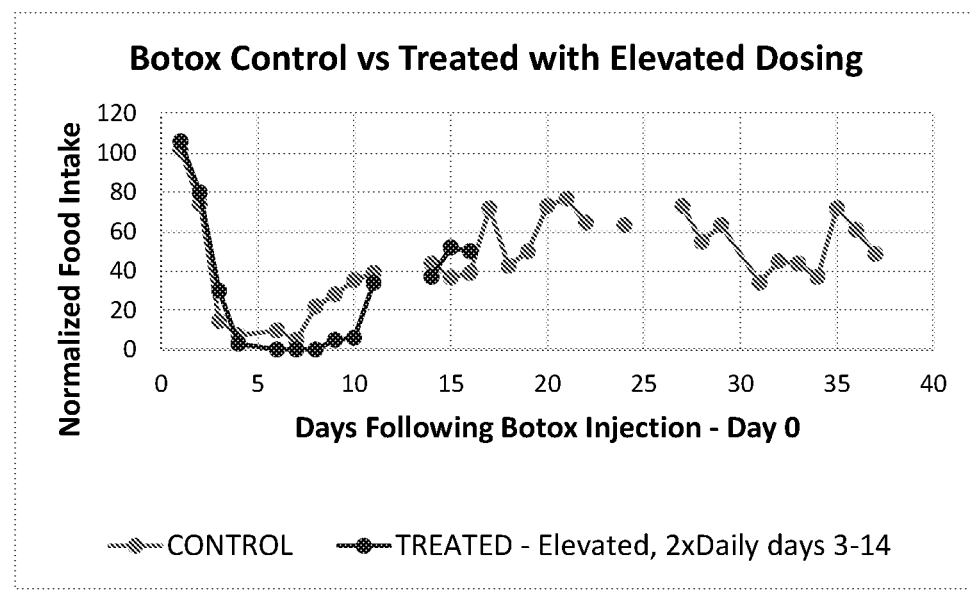
FIG. 5 is a line chart of the food intake after BOTOX injection of rats treated with an elevated dosing regimen of the anticholinesterase, and rats treated with no anticholinesterase.

FIG. 5 shows that the animals treated with an elevated dosing regimen experienced a lag in recovery of food intake. It is assumed that this lag in response is due to temporary poisoning of the endplate terminals. Recovery does not take place until 10+ days post BOTOX immobilization as compared to the BOTOX only control which starts to recover spontaneously after 6 days. Elevated dosing in this experiment was defined as a dose of twice daily injections of 0.25 mg per side starting from Day 3 up to Day 14.

CONCLUSION

In a human subject the rescue or reversal of a state of partial chemical denervation is expected to show a more rapid response. As previously explained the presence of naturally occurring acetylcholine is a precursor to establishing neurotransmission. The advent of side effects is known to occur as a result of spread of toxin which results in off-target effects. This is most likely due to off-target muscle relaxation (partial chemical denervation) as compared to complete muscle immobility or paralysis. Based on the rodent food intake rodent model, which shows lower sensitivity to a dose-response profile to the neurotoxin induced paralysis, one of skill in the art expects the results in human models to be more pronounced. This is because the actual condition in both cosmetic and medical applications of neurotoxin in humans is not expected to reach a state of complete immobility, and especially in the manifestation of side-effects. The target dose of neurotoxin is expected to induce a state of muscle relaxation. This would confer the presence of partial denervation as opposed to complete denervation. Also, human models do not require chewing. In the rodent food intake model, chewing is a complex process and may be impacted by a number of factors in driving motor function. As a result, a state of partial chemical denervation was not attainable. This limitation led to the delayed onset of response, as acetylcholine would not be available until the onset of nerve sprouting.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed is:

1. A method of restoring neuromuscular transmission by locally administering an effective dose of a composition comprising an anticholinesterase to a non-responsive muscle, wherein the non-responsive muscle has been previously exposed to botulinum toxin, wherein the composition is targeted locally and administered directly to the non-responsive muscle.

2. The method of claim 1, wherein the botulinum toxin is botulinum toxin type A-G.

3. The method of claim 2, wherein the botulinum toxin is botulinum toxin type A.

4. The method of claim 1, wherein the anticholinesterase is selected from one or more of neostigmine, edrophonium, pyridostigmine, physostigmine, rivastigmine, galantamine, and combinations thereof.

5. The method of claim 1, wherein the anticholinesterase is pyridostigmine.

6. The method of claim 1, wherein the anticholinesterase is of formula:

$$\text{(I)}$$

or a pharmaceutically acceptable salt thereof, wherein
Y is $CR_3$ or $N^+X^-R_4$, wherein X is a halogen;
$R_1$ is selected from hydrogen, $C_1$-$C_6$ alkyl, —CO(OH), —CO($C_1$-$C_6$ alkoxy), —CO($NH_2$), —CONH($C_1$-$C_6$ alkyl), and —CON($C_1$-$C_6$ alkyl)$_2$;
$R_2$ is hydrogen, or $R_2$ and $R_3$ together with the atoms to which they are attached form an optionally substituted heterocycle;
$R_3$ is selected from amino $C_1$-$C_6$ alkyl, ($C_1$-$C_6$ alkylamino) $C_1$-$C_6$ alkyl, (di $C_1$-$C_6$ alkylamino) $C_1$-$C_6$ alkyl, —$NH_2$, —NH($C_1$-$C_6$ alkyl), —N($C_1$-$C_6$ alkyl)$_2$, and —$N^+$($C_1$-$C_6$ alkyl)$_3X^-$; and
$R_4$ is selected from $C_1$-$C_6$ alkyl, hydroxy $C_1$-$C_6$ alkyl, or $C_1$-$C_6$ alkoxy $C_1$-$C_6$ alkyl.

7. The method of claim 1, wherein the composition is administered by intra-muscular injection.

8. The method of claim 1, wherein the composition is administered topically or transdermally.

9. The method of claim 8, wherein the transdermal administration is transdermal patch or transdermal gel.

10. The method of claim 1, wherein the composition is a sustained-release composition.

11. The method of claim 10, wherein the release is over a period of 1-day, 7-day, or 30-day, or any combination of these.

12. The method of claim 1, wherein the composition is one-phase gel composition further comprising 20 to 80% by weight of phospholipids and 0.1% to 65% by weight of water.

13. The method of claim 12, wherein the gel composition is extrudable through a needle having about 30 gauge to about 33 gauge.

14. The method of claim 1, wherein anticholinesterase is administered in a dose of about 0.05-0.5 mg/kg.

15. The method of claim 1, wherein anticholinesterase is administered in a low dose.

16. The method of claim 15, wherein the low dose is about $4/5$ to $1/50$ of the clinical dose of the anticholinesterase when dosed for said anticholinesterase's oral or intravenous use.

17. The method of claim 1, wherein anticholinesterase is administered in a dose of about 0.15-0.25 mg/kg.

18. The method of claim 1, wherein anticholinesterase is administered in a dose of about 0.2 mg/kg.

19. The method of claim 1, wherein anticholinesterase is donepezil.

20. The method of claim 1, wherein anticholinesterase is ambenonium.

21. The method of claim 1, wherein the anticholinesterase is a reversible anticholinesterase having a carbamate.

22. The method of claim 1, wherein the anticholinesterase is a reversible anticholinesterase having a tertiary ammonium.

23. The method of claim 1, wherein the anticholinesterase is a reversible anticholinesterase having a quaternary ammonium.

24. The method of claim 1, wherein the anticholinesterase is a reversible anticholinesterase having a carbamate and a tertiary ammonium.

25. The method of claim 1, wherein the anticholinesterase is a reversible anticholinesterase having carbamate and a quaternary ammonium.

26. The method of claim 2, wherein the botulinum toxin is botulinum toxin type B.

* * * * *